(12) United States Patent
Shigeura

(10) Patent No.: US 6,833,536 B2
(45) Date of Patent: Dec. 21, 2004

(54) NON-CONTACT RADIANT HEATING AND TEMPERATURE SENSING DEVICE FOR A CHEMICAL REACTION CHAMBER

(75) Inventor: John Shigeura, Portola Valley, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/359,668

(22) Filed: Feb. 6, 2003

(65) Prior Publication Data

US 2003/0231878 A1 Dec. 18, 2003

Related U.S. Application Data

(60) Provisional application No. 60/382,502, filed on May 22, 2000.

(51) Int. Cl.[7] ........................... G01N 25/00; H05B 1/02; B01J 19/08
(52) U.S. Cl. ........................ 219/553; 219/385; 219/411; 219/413; 219/428; 422/109; 422/186
(58) Field of Search .................. 219/385, 411, 219/413, 428, 494; 422/82.12, 109, 186, 121, 123, 130; 374/121, 123, 130

(56) References Cited

U.S. PATENT DOCUMENTS 4,632,908 A * 12/1986 Schultz ........................ 374/130
5,154,888 A 10/1992 Zander et al. ................. 422/58
5,232,667 A 8/1993 Hieb et al. ................. 422/82.04
5,288,463 A 2/1994 Chemelli ...................... 422/58
5,415,839 A 5/1995 Zaun et al.
5,422,271 A 6/1995 Chen et al. ................. 435/287
5,460,451 A 10/1995 Wadman
5,539,673 A 7/1996 Charm et al. ............... 364/557
5,653,537 A 8/1997 Ignatowicz et al. ......... 374/131
5,796,080 A 8/1998 Jennings et al.
5,863,801 A 1/1999 Southgate et al. ............ 436/63
5,882,903 A 3/1999 Andrevski et al. ......... 435/91.2
6,022,141 A * 2/2000 Bass ....................... 422/82.12
6,258,329 B1 7/2001 Mutterer, Jr. et al.
6,367,972 B1 4/2002 Kamiyama et al. ......... 374/133
2002/0047003 A1 * 4/2002 Bedingham et al. ........ 219/428

OTHER PUBLICATIONS

Roche Molecular Biochemicals, "LightCycler Operator's Manual," Version 3.5, Oct. 2000, pp. 13–29, and 95–101.
Copy of http://www.lightcycler-online.com/lightcycler-sys/instrum-menu.htm, May 13, 2002.
PCT International Search Report, International Application No. PCT/US03/12923 dated Oct. 2, 2003.

* cited by examiner

Primary Examiner—Joseph Pelham

(57) ABSTRACT

An apparatus and methods are provided for heating and sensing the temperature of a chemical reaction chamber without direct physical contact between a heating device and the reaction chamber, or between a temperature sensor and the reaction chamber. A plurality of chemical reaction chambers can simultaneously or sequentially be heated independently and monitored separately.

30 Claims, 3 Drawing Sheets

NON-CONTACT RADIANT HEATING AND TEMPERATURE SENSING DEVICE FOR A CHEMICAL REACTION CHAMBER

CROSS REFERENCE TO RELATED APPLICATION

The present application claims a benefit under 35 U.S.C. §119(e) from earlier filed U.S. Provisional Patent Application No. 60/382,502, filed May 22, 2002, which is incorporated herein in its entirety by reference.

FIELD

The present invention relates to an apparatus and method for heating and sensing the temperature of a chemical reaction chamber.

BACKGROUND

Temperature control is a common requirement for biochemical reactions. Conventional temperature control designs typically require some form of contact (e.g., physical engagement) or interconnection (e.g., electrical connectors) between an instrument and one or more discrete reaction devices to perform the temperature control functions.

Such contact or interconnection, however, is not always practical or desirable. For various purposes, a non-contact radiant heating and temperature sensing device for a chemical reaction chamber may be desirable.

All patents, applications, and publications mentioned here and throughout the application are incorporated in their entireties by reference herein and form a part of the present application.

SUMMARY

Various embodiments provide a system that includes a non-contact radiant heater and a non-contact temperature sensor for a chemical or biochemical reaction chamber. The heater can be designed to emit radiation having a wavelength of, for example, about 0.7 micrometer or longer, or about 1.5 micrometers or longer. The heater can be, for example, a laser source or a halogen light source. The sensor can detect radiant energy emitted from the reaction chamber without contacting the reaction chamber. According to various embodiments, the sensor can detect radiant energy having a wavelength of from about two micrometers to about 20 micrometers, for example, a wavelength of from about five micrometers to about 15 micrometers. The sensor can be, for example, a non-contact infrared pyrometer.

According to various embodiments, a non-contact heating and temperature sensing system is provided for regulating temperature within a chemical reaction chamber. The reaction chamber can be formed in a substrate or can be fixed, secured, mounted, or otherwise attached or connected to a surface of a substrate or to a holder.

According to various embodiments, a method is provided whereby a non-contact radiant energy source is used to heat a reaction region to effect or promote a chemical and/or biochemical reaction. The reaction region can be within an analytical instrument such as a polymerase chain reaction (PCR) device, a medical diagnostic device, a DNA purification instrument, a protein or blood gas analyzer, or other instrument. The energy source can be designed to emit energy having a wavelength sufficient to carry out a desired reaction or desired reaction rate. For example, according to various embodiments, the energy source emits energy having a wavelength of at least about 0.7 micrometer.

It is to be understood that both the foregoing description and the following description are exemplary and explanatory only, and are not limiting.

DESCRIPTION OF VARIOUS EMBODIMENTS

When energy is radiated from an object, the radiated energy can be used according to various embodiments to make a determination of the temperature of the object. The energy can be in the visible light spectrum or in the non-visible light spectrum. As the energy strikes a detector in a sensor, a reaction occurs that can result in an electrical signal output from the detector. The electrical output can be a signal that can be processed, for example, amplified and/or linearized, as desired, to calculate temperature according to common pyrometer techniques.

Some applicable circuits, signal processing systems, temperature sensors, heaters, and related devices that can be useful in constructing a system according to various embodiments are described in U.S. Pat. Nos. 4,632,908; 5,232,667; 5,653,537; 5,882,903; 5,539,673; and 6,022,141, which are incorporated herein in their entireties by reference.

Figure 1:
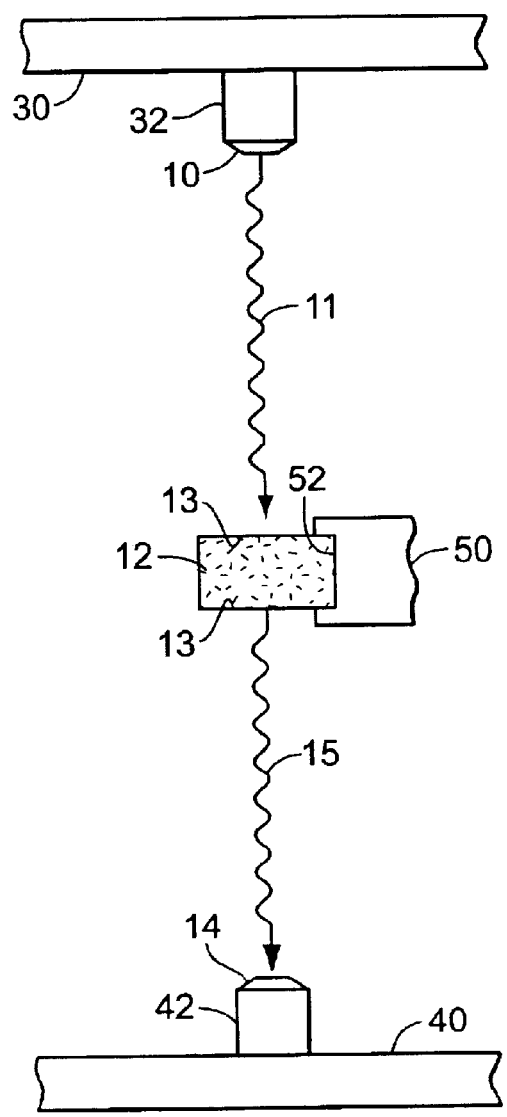
FIG. 1 is a schematic view of a radiant heater, biochemical reaction chamber, and radiant temperature sensor according to various embodiments.

According to various embodiments, a heating and temperature-sensing system is provided, for example, as shown in FIG. 1. The system of FIG. 1 includes a first platform, first platform region, or radiant heater platform 30 that includes a heater support 32 supporting a non-contact radiant heater 10. The non-contact radiant heater 10 can emit radiant energy 11 in a direction toward a chemical reaction chamber 12. The reaction chamber 12 can be an individual chamber defined by sidewalls 13 or can be formed in a substrate of an assembly or device (not shown in FIG. 1). The reaction chamber 12 can be supported by a device support 50 that can include a holding feature such as, for example, a recess 52 as shown, for receiving and supporting the reaction chamber 12 for heating the reaction chamber 12. The holding feature instead or additionally includes a clamp, a threaded rod or threaded hole, a magnetic attachment device, a suction or vacuum holding device, a snap-fit connection, a recess in a spinnable platen, or any other holding feature that would be apparent to one skilled in the art. The system can further include a second platform or second platform region 40 having a support 42 for supporting a non-contact radiant temperature sensor 14. Radiant energy 15 emitted from the heated reaction chamber 12 radiates at least in a direction toward the non-contact temperature sensor 14 and is detected by the temperature sensor 14.

According to various embodiments of the present invention, the radiant heater 10 can heat the reaction chamber 12 without physically contacting the reaction chamber 12 or a reaction mixture in the reaction chamber 12. The temperature sensor 14 can sense the temperature of the reaction chamber 12 and/or the contents of the reaction chamber 12 via radiant energy emissions without contacting the reaction chamber 12.

The radiant heater 10 can be spaced away from the reaction chamber 12 by a distance of, for example, from about one millimeter to about 10 cm, or more. The radiant heater 10 can be spaced away from the reaction chamber 12 a distance of at least about two millimeters, for example, a distance of from about five millimeters to about 20 mm away from the reaction chamber 12.

The temperature sensor 14 can be spaced away from the reaction chamber 12 by a distance of, for example, from about one millimeter to about 10 cm, or more. The temperature sensor 14 can be spaced away from the reaction chamber 12 a distance of at least about two millimeters, for example, a distance of from about five millimeters to about 20 mm away from the reaction chamber 12.

The distance of the radiant heater 10 from the reaction chamber 12 can be the same as, or different than, the distance of the temperature sensor 14 from the reaction chamber 12.

The device support 50, non-contact radiant heater support 32, and the temperature sensor support 42, can be commonly secured, mounted, affixed, or otherwise attached to a common structure, such as the housing for a work station. Exemplary work stations that can include various supports, whether or not directly or indirectly mounted to the work station housing, include devices to carry out PCR. Other exemplary work stations or platforms that can be used or adopted for use include, for example, devices to heat-treat a heat-curable material such as glue disposed between components of an assembly, and other instruments that require heating.

The reaction chamber 12 can be adapted to hold samples, for example, fluids that can include, for example, polynucleotide primers, polynucleotide probes, nucleic acids, deoxyribonucleic acids, dideoxyribonucleic acids, ribonucleic acids, peptide nucleic acids, individual polynucleotides, buffers, other ingredients known or used in conjunction with PCR techniques, and combinations thereof. The reaction chamber 12 can be sealed sufficiently to prevent or minimize evaporation and contamination of a liquid sample, such as a PCR fluid, disposed in the reaction chamber.

Herein, the "chemical reaction chamber" and "reaction chamber" can include, for example, any chamber, vessel, container, sample well, purification tray, microtiter tray, capsule, sample array, centrifuge tube, or other containing, retaining, restraining, or confining device, without limitation, that is able to retain one or more chemicals or biochemicals for a reaction thereof. The reaction chamber can be formed in a substrate or can be fixed, secured, mounted, or otherwise attached or connected to a surface of a substrate or to a holder.

The reaction chamber can have a cylindrical shape, a cubical shape, a rectangular shape, a parallelepiped shape, or any other shape. The reaction chamber can comprise a reaction chamber in a microanalytical device such as a card-type assay device. The volume of the reaction chamber can be, for example, from about 1 $\mu$l to about 10 ml, from about 0.1 $\mu$l to about 1 ml, from about 0.1 $\mu$l to about 100 $\mu$l, or from about 0.1 $\mu$l to about 10 $\mu$l.

The reaction chamber can have at least one dimension of about 600 $\mu$m or less, for example, a reaction chamber having at least one dimension of about 500 $\mu$m or less, or of about 400 $\mu$m or less, or of about 300 $\mu$m or less. For example, the reaction chamber can be cylindrical in shape, can have a diameter of from about 0.5 mm to about 3.0 mm, for example, from about 1.0 mm to about 2.0 mm, and a depth of from about 100 $\mu$m to about 600 $\mu$m, for example, from about 200 $\mu$m to about 500 $\mu$m.

According to various embodiments, the system can include a plurality of non-contact radiant heaters, a plurality of non-contact temperature sensors, or a plurality of both. One reaction chamber can be heated and temperature-sensed according to various embodiments of the present invention, or a plurality of reaction chambers can be heated simultaneously or sequentially and/or sensed simultaneously or sequentially.

The temperature range of the radiant heating device according to various embodiments can be from about 20° C. up to and including about 100° C., and can encompass the typical temperature ranges needed for conventional biochemical reactions, for example, temperatures desirable for PCR reactions, for example, between about 60° C. and about 95° C.

The radiant heating source according to various embodiments can operate to generate radiation in the infrared or near infrared region of the electromagnetic radiation spectrum, for example, wavelengths of equal to or greater than about 0.5 micrometer, for example, equal to or greater than about 0.7 micrometer. The temperature sensor device of the present invention can, according to various embodiments, detect temperatures in the infrared region of the electromagnetic radiation spectrum, that is, radiant energy of wavelengths of at least about five micrometers, for example, from about five micrometers to about 15 micrometers.

According to various embodiments, the radiant heater can comprise a laser source, a halogen bulb, a lamp heater, and/or a photon or light source heater that emits radiation having a wavelength of at least about 0.5 micrometer or greater, for example, at least about 0.7 micrometer. The radiant heater can unidirectionally emit a radiation beam toward the reaction chamber. According to such embodiments, the unidirectional emission avoids wasting energy due to emissions in directions not toward the reaction chamber.

The temperature sensor, according to various embodiments, can be a thermopile and/or any other suitable optical temperature-sensing device.

Figure 2:
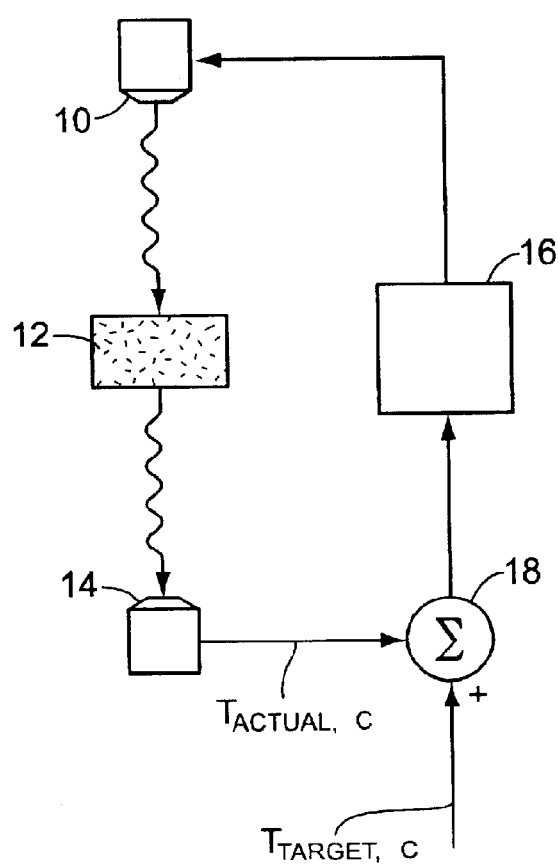
FIG. 2 is a schematic drawing of a radiant heater, biochemical reaction chamber, radiant temperature sensor, and control system according to various embodiments.

FIG. 2 shows a temperature control system according to various embodiments of the present invention that can be used to carry out methods according to various embodiments. FIG. 2 shows a non-contact radiant heater 10, a chemical reaction chamber 12, a temperature sensor 14, and a temperature control system 16. Also shown in FIG. 2 is a control mechanism 18 that is adapted to measure the actual temperature ($T_{actual}$) detected from the reaction chamber, for example, in degrees Centigrade (° C.), and is adapted to respond to a signal for a desired or target temperature ($T_{target}$), for example, in degrees Centigrade.

According to various embodiments, the control unit 18 can be, for example, a CPU or other processor or microprocessor. The control unit can be adapted to determine, based on detector responses received from the temperature sensor, and/or in combination with the temperature sensor, the temperature of the reaction chamber. The reaction chamber temperature can be determined from radiant energy exiting the reaction chamber through, for example, a transparent film or transparent wall that at least partially defines the reaction chamber. The temperature of the reaction chamber can be determined from a measured radiant energy radiating from a black or opaque film, or a black or opaque wall, that at least partially defines the reaction chamber. The control unit 18 can receive a signal from the temperature sensor indicating the temperature of the reaction chamber, and optionally can also record the temperature detected. The control unit 18 can be a computer (e.g., a programmed general computer, or a special purpose computer) or a microprocessor adapted to send a command to the radiant heater to begin, increase, maintain, decrease, or end the radiant heat emission or output of the radiant heater. The control unit 18 can therefore be provided with a microprocessor on which, or within which, is embedded a software program for receiving and/or responding to signals or to pre-set conditions for temperature maintenance. The radiant heater can be adapted or controlled with the control unit to receive signals from the control unit 18, and respond accordingly to begin, increase, maintain, decrease, or end the heat energy output.

According to various embodiments, the control unit 18 can also include a timer or a time-keeping program, or can be used in conjunction with a timer or a time-keeping program. The control unit 18 can be programmed to control the radiant output of the non-contact radiant heater based on a signal provided by the temperature sensor, the timer, the time-keeping program, or a combination thereof.

Figure 3:
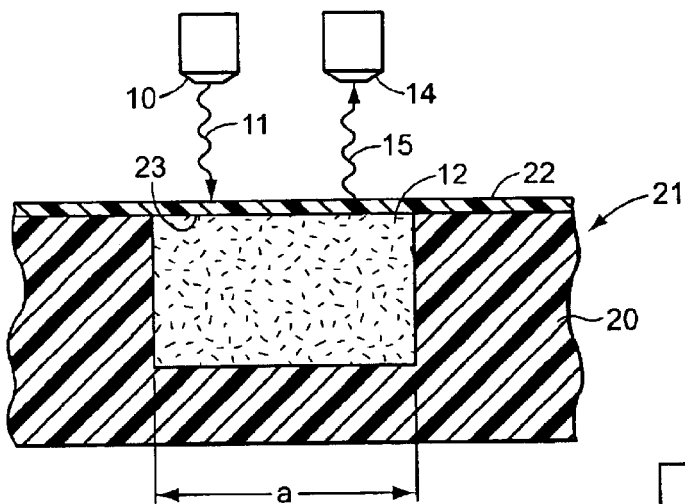
FIG. 3 is a cross-sectional view of a biochemical reaction chamber formed in a device substrate and having an aluminum film cover, according to various embodiments.

FIG. 3 shows a system according to various embodiments that includes a chemical reaction chamber 12 having a length "a" that can be from about one micrometer up to and exceeding one centimeter, for example, from about one to about two millimeters. The dimension "a" can be a diameter if the reaction chamber is round, or a length if the reaction chamber is linear, square, rectangular, or the like. As in the embodiment of FIG. 1, the reaction chamber 12 can be formed in a substrate 20 of an assembly 21.

According to various embodiments, materials useful for the assembly of substrate 20 include those having structures and/or comprised of materials that together provide a low thermal conductivity, for example, structures including a reaction chamber width (or diameter) to sidewall depth ratio of greater than 1:1, and materials having a thermal conductivity of below about 1.0 W/m° C. Materials that can be used for the substrate include, for example, polycarbonate, other plastics, glass, other thermally resistant materials, and combinations thereof.

According to various embodiments, the reaction chamber 12 can be closed on the top by a thin cover 22. The cover 22 can be rigid or flexible. The cover 22 can be optically transparent, translucent, or opaque, for example, black in color. In various embodiments wherein the reaction chamber is at least partially defined by a cover, the cover can have, for example, a high thermal conductivity, e.g., a thermal conductivity of greater than about 1.0 W/m° C., and an emissivity of about 0.1 or higher, for example, about 0.5 or higher, on a scale of from zero to one. Such materials can include, for example, an aluminum film blackened on the top by anodizing, painting, or some other coating material or technique, or a thin black plastic film such as a pigmented polycarbonate. Because black-anodized aluminium has a high thermal conductivity (e.g., 1.0 W/m° C. or greater), it can be used as a thin or thick film cover, for example, as a film cover having a thickness of from about 0.01 mm to about 1.0 mm or greater. A rigid plate, for example, made of pigmented polycarbonate, can be used as the cover 22. Materials of low thermal conductivity (e.g., less than 1 W/m° C.) can be used as thin film covers provided they are thin enough to exhibit a suitable thermal conductivity, for example, an optically transparent polycarbonate film having a thickness of from about 0.01 mm to about 1.0 mm, for example, a thickness of from about 0.01 mm to about 0.5 mm.

Radiant energy can be used to heat the chemical materials by conduction through the cover 22 or by transmission of radiant energy through the cover in situations where, for example, the cover comprises an optically transparent or optically translucent material. Black or opaque covers that absorb heat from the non-contact radiant heater can be used and can heat-up and conduct heat to components in a reaction chamber at least partially defined by the cover. The bottom surface 23 of the cover 22 can be in direct contact with a reaction liquid or materials in the reaction chamber 12.

In the embodiment shown in FIG. 3, the radiant energy source 10 can emit radiation toward cover 22. In various embodiments, the cover 22 can be black or opaque and can absorb heat from the non-contact radiant heater, then conduct the heat to the underlying or adjacent reaction chamber and components therein. In various embodiments, the cover 22 can be optically transparent or optically translucent and can transmit heat radiated from the non-contact radiant heater through the cover 22, and heat the reaction chamber or components therein without the need to conduct heat from the cover 22 into the reaction chamber. In various embodiments, the cover 22 is removed or absent and the radiation from the radiant energy heating source 10 strikes and heats directly the chemical materials in the reaction chamber 12, or strikes and heats the desired materials after passing through a transparent, non heat-absorbing film or other cover. According to various embodiments, there is no direct physical contact between the radiant energy heating source 10 and either the reacting materials in reaction chamber 12 or the cover film 22.

The temperature sensor 14 shown in FIG. 3 can operate on the same side of the substrate 20 as the heating source 10, as shown. The sensor can sense or detect the temperature of the cover 22 that in turn is about the same as, or correlates in a known manner to, the temperature in the interior of the reaction chamber 12.

Figure 4:
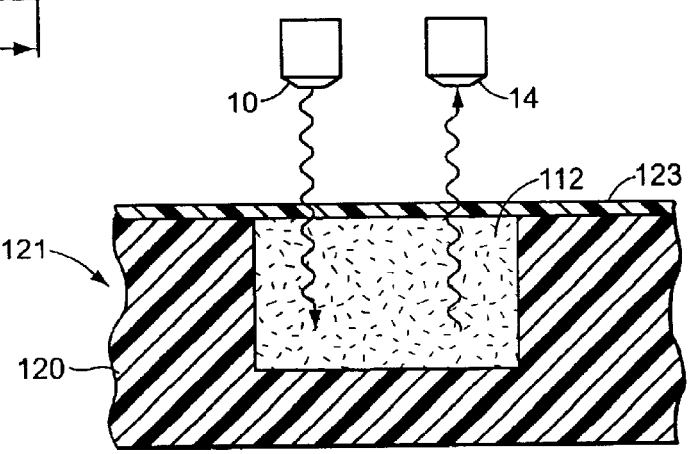
FIG. 4 is a cross-sectional view of a biochemical reaction chamber formed in a device substrate and having a transparent film cover, according to various embodiments.

FIG. 4 shows another embodiment, including an assembly 121 having a reaction chamber 112 similar to the chamber 12 shown in FIG. 3. The assembly 121 includes a thin transparent film cover 123. The film cover 123 can include a transparent film, for example, of polycarbonate, polyethylene, polyester, polypropylene, other plastics, copolymers, composites thereof, combinations thereof, and the like. According to the embodiment of FIG. 4, radiant energy passes through the transparent cover film 123 from a radiant heater 10 to heat reacting material contained beneath the cover 123 and within the reaction chamber 112 in substrate 120. A temperature sensor 14 detects radiation emitted from the reaction chamber 112 that radiates outwardly through the cover 123. The cover film 123 can, according to various embodiments, be of any suitable thickness, for example, less than or equal to 2.0 mm, or less than 1.0 mm. According to various embodiments wherein the cover 123 is optically transparent or optically translucent, the cover can exhibit an emissivity high enough to transmit radiant heat indicative of the temperature of the reaction chamber from the reaction chamber toward the non-contact radiant temperature sensor.

According to various embodiments wherein the cover 123 is black or opaque, the cover can exhibit an emissivity high enough to absorb heat from the reaction chamber and, in turn, radiate heat indicative of the temperature of the reaction chamber toward the non-contact radiant temperature sensor. The cover 123 can have an emissivity of about 0.1 or higher, for example, about 0.5 or higher, or 0.75 or higher, on a scale of from zero to one. Such materials can include, for example, an aluminum film blackened on the top by anodizing, painting, or some other coating material or technique, or a thin black plastic film such as a pigmented polycarbonate.

Figure 5:
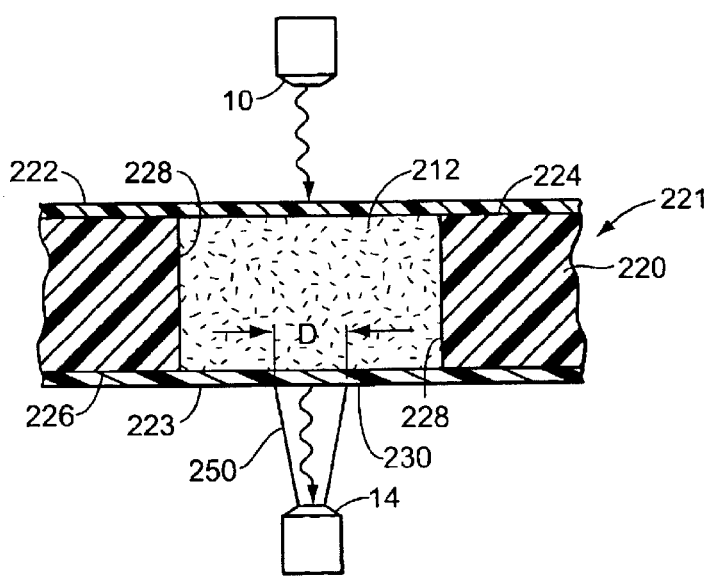
FIG. 5 is a cross-sectional view of a biochemical reaction chamber formed in a device substrate and having a transparent film cover on both sides of the device, according to various embodiments.

FIG. 5 is a cross-sectional view of an assembly 221 including a chemical reaction chamber 212 having a film cover 222 and a film cover 223. The materials for covers 222 and 223 can be, for example, optically transparent, optically translucent, opaque, black, or a combination thereof, as described in connection with FIGS. 3 and 4. The film cover 222 can be, for example, an optically transparent or optically translucent film on the top side 224 of the substrate 220, and the film cover 223 can be, for example, an opaque or black film cover 223 on a bottom side 226 of the substrate 220. FIG. 5 depicts the chemical reaction chamber 212 as a through-hole 228 in the substrate 220. The through-hole 228 is sealed with the covers 222 and 223. The radiant heater 10 and temperature sensor 14 can be placed on opposite sides of the assembly 221 and can be located at different positions of the reaction chamber. According to various embodiments, the radiant heater 10 and the temperature sensor 14 are coaxially aligned and in use can be used in an alternating manner such that the temperature sensor can sense the temperature of the reaction chamber while the non-contact radiant heater is not heating the reaction chamber.

As shown in FIG. 5, the non-contact temperature sensor 14 receives radiant energy from directions encompassed by a line of sight or field of view 250. According to various embodiments, the field of view 250 of the non-contact radiant temperature sensor 14 can diverge conically toward the reaction chamber 212 and intersect with a first surface 230 of film cover 223 in an area having a diameter D referred to herein as the field of view viewing area. The field of view can intersect the reaction chamber or an outer wall thereof in a viewing area having a shape other than circular, but having a diameter. To minimize background radiation that can affect or distort the temperature sensed by non-contact temperature sensor 14, the periphery of the field of view of the sensor can be wholly encompassed by a surface. For example, the periphery of the field of view can (e.g., an outer surface) of the reaction chamber being sensed. For example, the periphery of the field of view can fall wholly on a portion of a film cover surface that defines the reaction chamber, as shown in FIG. 5.

The field of view viewing area at the surface of the reaction chamber can be smaller than the area of the reaction chamber wall or surface being temperature-sensed. The field of view viewing area can wholly fall within a corresponding reaction chamber or reaction chamber surface having an optically transparent or optically translucent film cover that is adjacent the reaction chamber. The field of view viewing area can have an area that is larger, smaller, or the same area as the area of a corresponding reaction chamber surface or reaction chamber film cover surface to be temperature-sensed. The ratio of the field of view viewing area to the reaction chamber surface area can be from about 2:1 to about 1:20, for example, from about 1:10 to about 9:10, from about 1:6 to about 1:2, or from about 1:5 to about 1:3. The field of view viewing area can have a diameter or smallest dimension, for example, of from about 0.1 mm to about 10 mm or greater, for example, a diameter or smallest dimension of from about 0.5 mm to about 5 mm, or from about 1.0 mm to about 2.0 mm. Exemplary non-contact radiant heaters that can be used according to various embodiments include those described in U.S. Pat. Nos. 5,232,667 and 6,367,972, which are incorporated herein in their entireties by reference. Exemplary sensors that can be used include infrared sensors having a focused line of sight.

According to various embodiments, the reaction chamber can be within a device that is covered with a cover, such as, but not limited to, a metal cover. Exemplary metal covers for the reaction chamber include a black aluminum cover that can receive radiant energy from the radiant heater, according to various embodiments.

In various embodiments, the reaction chamber can be in a device that is covered, at least in part, with a transparent film. Thin films, such as films of 0.1 mm thickness or less, are useful as covers for the reaction chamber of various embodiments. Such a thin film can comprise, but is not limited to, a plastic such as polycarbonate, or any other material optically transparent to a wavelength, that is, which transmits about 100% of the energy of the wavelength desired for heating reactants in the chemical reaction chamber.

The assembly designs depicted in FIGS. 3–5 can accommodate, according to various embodiments, two or more chemical reaction chambers. Heating and temperature sensing of a plurality of chemical reaction chambers together can be accomplished by various embodiments. Each reaction chamber of a plurality of reaction chambers can be moved in turn under a single non-contact radiant heater, or can be aligned with a respective non-contact radiant heater. Each reaction chamber of a plurality of reaction chambers can be lined up with a temperature-sensing device, or each reaction chamber of a plurality of reaction chambers can be lined-up with a respective temperature sensor. According to various embodiments, a plurality of reaction chambers can be arranged in a heatable device, for example, a microfluidic analytical device such as a microcard device, and together rotated about an axis of rotation central to the heatable device or a platform holding the device. An example of such a device is shown in FIG. 6.

Figure 6:
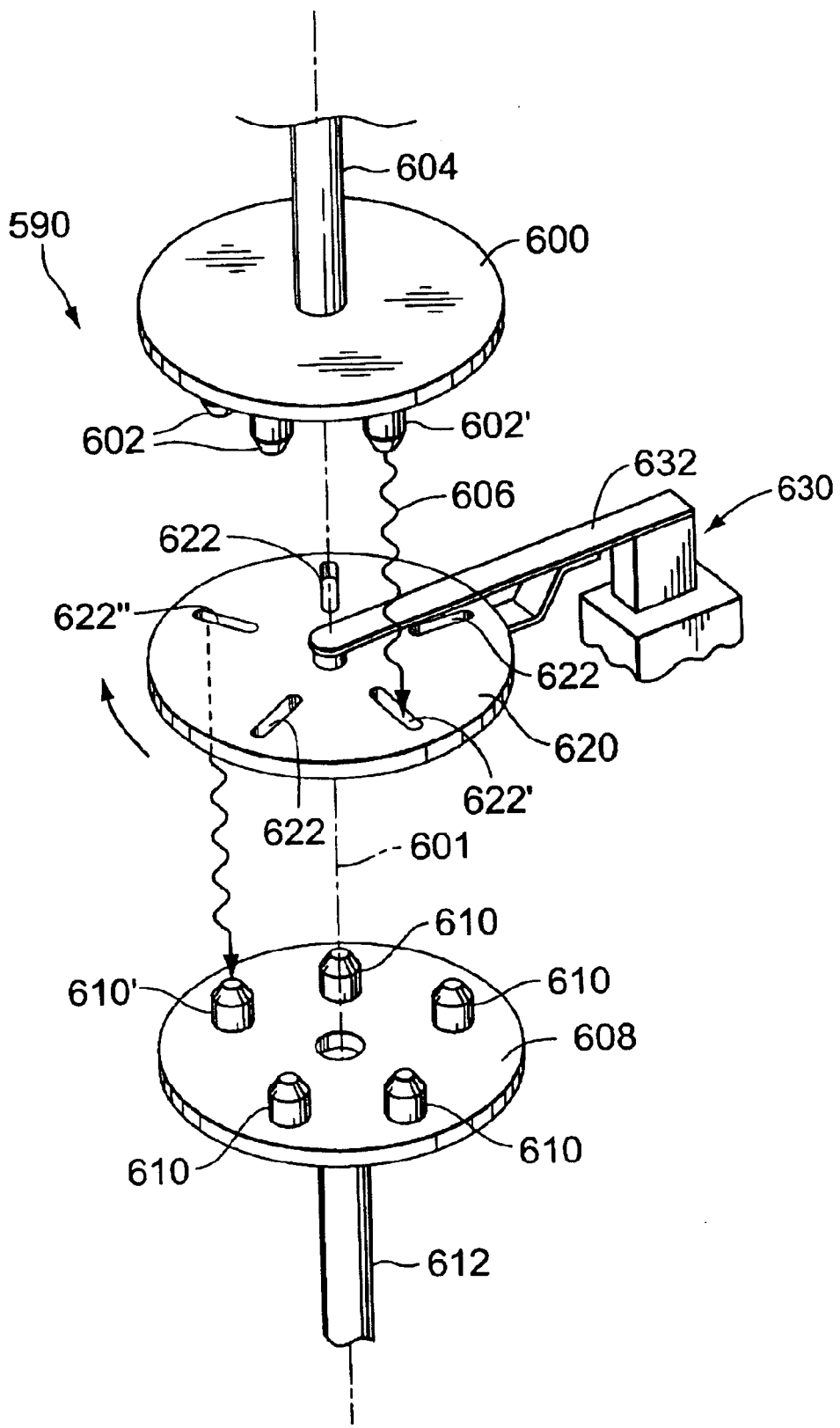
FIG. 6 is a perspective exploded view of a rotating non-contact heating and temperature-sensing system according to various embodiments.

In various embodiments, a non-contact radiant heating and temperature-sensing system 590 is provided, as shown in FIG. 6. The system 590 can include a rotatable heating assembly 600. Any number of individual non-contact radiant heaters 602 can be mounted, fixed, connected, attached, or otherwise supported by or secured to the heater assembly 600. The heater assembly 600 can be rotated about an axis of rotation 601 on a shaft 604. An appropriate motor and drive system can be provided to rotate the shaft 604 and corresponding heater assembly 600 as desired. Appropriate circuitry and electronics can be provided to selectively activate one or more of the individual heaters 602 of the heater assembly 600 and/or to coordinate a sequence of activations of the various heaters. In FIG. 6, non-contact radiant heater 602' is the only heater of the heater assembly 600 that is shown emitting radiant heat 606 in the drawing. Radiant heat 606 can be directed, for example, by rotation of heater assembly 600, so as to radiate, for example, linearly, toward a reaction chamber 622'.

Reaction chamber 622' can be one of a plurality of reaction chambers 622 in a reaction chamber assembly 620.

Although the heater assembly 600 can be spaced-apart from the reaction chamber assembly 620 in the proportions shown in FIG. 6, FIG. 6 is an exploded view of the system 590, and the distance between heater 602' and reaction chamber 622' can be from about 0.1 mm to about 100 mm, for example, from about 1 mm to about 30 mm, or from about 5 mm to about 20 mm. Reaction chamber assembly 620 can be supported for rotation about axis of rotation 601 by a support device 630 that can include a support arm 632, a motor, and transmission components (not shown) to rotate the reaction chamber assembly 620. Motor and transmission components can be provided that rotate the reaction chamber assembly 620 to position one or more of the reaction chambers 622 with respect to one or more of the non-contact radiant heaters 602, and/or to spin the reaction chamber assembly 620 at rpms sufficient to effect a centripetal manipulation of a sample in a reaction chamber. The reaction chamber assembly can be spun at speeds of 100 rpm or greater, for example, speeds of 1000 rpm or greater, 3000 rpm or greater, or 5000 rpm or greater.

According to various embodiments, a heated reaction chamber 622" can be temperature-sensed by a non-contact radiant temperature sensor 610' at the same time that the non-contact radiant heater 602' heats reaction chamber 622'. Non-contact radiant heater 602' can be activated at the same time that sensor 610' is activated so that heat from reaction chamber 622' does not distort sensing of temperature by sensor 610'. Non-contact radiant temperature sensor 610' can be one of many temperature sensors 610 commonly supported, mounted, connected, attached, or otherwise affixed or secured to a temperature-sensing assembly 608. Although the temperature-sensing assembly 608 can be spaced-apart from the reaction chamber assembly 620 in the proportions shown in FIG. 6, FIG. 6 is an exploded view of the system 590. The temperature-sensing assembly 608 can be spaced, for example, from about 0.1 mm to about 100 mm away from the reaction chamber assembly 620, for example, from about 1 mm to about 30 mm, or from about 5 mm to about 20 mm away from the reaction chamber assembly 620. Temperature-sensing assembly 608 can be rotated about the axis of rotation 601 by a motor and transmission system that rotates a shaft 612 attached to the temperature-sensing assembly 608 for rotation of the same.

Each of the heater assembly 600, reaction chamber assembly 620, and temperature sensing assembly 608 can independently be stationary or rotatable. For example, one or more of these three assemblies or all three assemblies, can be rotated about an axis of rotation 601 to effect any of various alignments of the non-contact radiant heaters 602 and/or the non-contact temperature sensors 610 with the various reaction chambers 622. One or more of the heater assembly 600, reaction chamber assembly 620, and temperature sensing assembly 608 can be provided with a rotatable platform so that one or more of the heater assembly 600, reaction chamber assembly 620, and temperature sensing assembly 608 can be rotated individually or jointly about axis of rotation 601, as shown. One or more of the heater assembly 600, reaction chamber assembly 620, and temperature sensing assembly 608 can be stationarily supported on, for example, a platform or a support, for example, shaft 604 as shown in FIG. 6. A control system can be included to activate one or more of the non-contact radiant heaters 602 in response to a signal provided indicative of one or more temperatures of one or more of the reaction chambers 622. A plurality of the non-contact radiant heaters can be activated sequentially or simultaneously in response to detected temperatures of a corresponding plurality of reaction chambers 622.

According to various embodiments such as shown in FIG. 6, the system can heat and control the temperatures of the plurality of chemical reaction chambers individually. The plurality of reaction chambers can be individually cooled, or cooled together by any of a variety of cooling apparatus and methods. For example, cool or ambient air or fluid can be directed toward the reaction chambers, a cooling fan can be provided to blow a cooling fluid at the reaction chambers, the reaction chambers can be spun and cooled by the spinning action in ambient or cool air, the reaction chambers can be immersed in a cooling liquid, the reaction chambers can cooled by conduction against a cooling surface, or any other suitable cooling device or cooling method can be used. Such a design also allows each reaction chamber to be monitored individually. An assembly can be provided, according to various embodiments, wherein a separate radiant heater and a separate heat sensor are provided for each of a plurality of reaction chambers. The radiant heater can be position mounted on a static or on a movable platform. The heat sensor can be position mounted on a static or a movable platform.

In embodiments such as those shown in FIGS. 3–5, and wherein multiple heaters and sensors are used, the radiant or optical heating sources 10 and the temperature sensors 14 can be operated either simultaneously or alternately. Alternate operation of the heater 10 and sensor 14 can be used to reduce detection by the sensor of radiation that might be reflected by a cover in embodiments where a non-contact radiant heater and a non-contact temperature sensor are used on the same side of a reaction chamber. Alternate heating and temperature sensing can also reduce or eliminate the sensing of radiant heat emanating from the non-contact radiant heater and not from the reaction chamber.

According to various embodiments, method of non-contact heating and temperature sensing are provided for conducting a chemical reaction. For example, the method can involve (i) directing radiation towards a reaction mixture from a radiant heating source spaced away from the reaction mixture; (ii) detecting radiation emanating from the reaction mixture, and (iii) determining the temperature of the reaction mixture based on the detected radiation. The method can include directing radiation toward a reaction mixture in a reaction chamber having a volume of less than about 10 ml, for example, having a volume of from about 1.0 $\mu$l to about 10 $\mu$l. The method can include detecting radiation with a temperature sensor having a field of view viewing area diameter of from about 0.1 mm to about 10 mm, for example, of from about 1.0 mm to about 2.0 mm. The method can include directing radiation toward a reaction mixture in a reaction chamber having at least one dimension of about 600 $\mu$m or less, for example, a reaction chamber having at least one dimension of about 500 $\mu$m or less, of about 400 $\mu$m or less, or of about 300 $\mu$m or less.

According to various embodiments, a method can be provided that can include providing a non-contact heating and temperature sensing system for a chemical reaction chamber, wherein the system can include: i) a source of radiant energy that emits radiation having a wavelength of at least about 0.7 micrometer; ii) a temperature sensor able to detect radiant energy without contacting the source of the radiant energy, wherein the sensor can detect a wavelength of at least about five micrometers; and (iii) a chemical reaction chamber arranged to receive radiant energy emitted from the source and to emit radiant energy toward the sensor.

According to various embodiments, the method can include providing one or more chemical or biochemical materials in the chemical reaction chamber, causing the source of radiant energy to emit radiation with a wavelength of at least about 0.7 micrometer in at least a direction toward the reaction chamber, whereby the emitted radiation directly or indirectly irradiates, illuminates, or otherwise heats the chemical or biochemical materials in the chemical reaction chamber, and measuring the temperature of the chemical or biochemical materials by detecting the radiant energy emitted from the chemical or biochemical materials with the temperature sensor.

According to various embodiments of the present invention, the radiant heating and sensing methods allow two or more chemical reaction chambers to be maintained simultaneously at different temperatures. The system for such a method can include a control unit for controlling various heaters and various temperatures simultaneously.

The radiant heating and temperature sensing is not dependent upon contact between a chemical reaction device and thermal components. The non-contact technique allows a heatable device to be easily moved inside a chemical reaction instrument or system and to be easily removed from the instrument or system. The heatable device can also be easily replaced after use.

In other various embodiments, a plurality of reaction chambers is conveyed to and from heating and temperature sensing regions on a continuous belt or line, such as on a conveyor belt.

Other embodiments of the present invention will be apparent to those skilled in the art from consideration of the specification and practice of the invention disclosed herein. It is intended that the specification and examples be considered as exemplary only.

What is claimed is:

1. A heating system comprising:
   a non-contact radiant heater;
   a non-contact radiant temperature sensor; and
   a heatable device including a chemical reaction chamber, the heatable device being spaced from the non-contact radiant heater a distance of from about five mm to about 20 mm, being spaced from the non-contact radiant temperature sensor a distance of from about five to about 20 mm, and positioned for the chemical reaction chamber to receive heat irradiated by the non-contact radiant heater and for the chemical reaction chamber to radiate heat toward the non-contact radiant temperature sensor.

2. A heating system comprising:
   a non-contact radiant heater;
   a non-contact radiant temperature sensor; and
   a heatable device including a chemical reaction chamber having at least one sample-confining dimension of about 600 $\mu$m or less, the heatable device being spaced from the non-contact radiant heater, spaced from the non-contact radiant temperature sensor, and positioned for the chemical reaction chamber to receive heat irradiated by the non-contact radiant heater and for the chemical reaction chamber to radiate heat toward the non-contact radiant temperature sensor.

3. A heating system comprising:
   a non-contact radiant heater;
   a non-contact radiant temperature sensor; and
   a heatable device including a chemical reaction chamber including a sidewall having an outer surface of a first area, the heatable device being spaced from the non-contact radiant heater, spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the non-contact radiant temperature sensor has a field of view that intersects the outer surface of the sidewall at a second area that is smaller than the first area.

4. A method of heating a biochemical sample comprising:
   providing a heatable device that includes a reaction chamber retaining a sample, the reaction chamber having at least one sample-confining dimension of about 600 $\mu$m or less;
   heating the reaction chamber with a non-contact radiant heater spaced from the heatable device; and
   sensing a temperature of the reaction chamber with a non-contact temperature sensor spaced from the heatable device.

5. A method of heating a biochemical sample comprising:
   providing a heatable device that includes a reaction chamber retaining a sample;
   heating the reaction chamber with a non-contact radiant heater spaced from the heatable device a distance of from about five mm to about 20 mm; and
   sensing a temperature of the reaction chamber with a non-contact temperature sensor spaced from the heatable device a distance of from about five mm to about 20 mm.

6. A heating system comprising:
   a non-contact radiant heater;
   a non-contact radiant temperature sensor;
   a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor; and
   a first platform region supporting the non-contact radiant heater, and a second platform region supporting the non-contact radiant temperature sensor, wherein a plurality of non-contact radiant heaters are supported by the first platform region, and a plurality of non-contact radiant temperature sensors are supported by the second platform region.

7. A heating system comprising:
   a non-contact radiant heater;
   a non-contact radiant temperature sensor; and
   a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the heatable device is spaced away from the non-contact radiant heater by a distance of from about five mm to about 20 mm.

8. A heating system comprising:
   a non-contact radiant heater;
   a non-contact radiant temperature sensor; and
   a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the non-contact radiant heater comprises a laser source.

9. A heating system comprising:

a non-contact radiant heater;

a non-contact radiant temperature sensor; and a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the non-contact radiant heater comprises a halogen light source.

10. The heating system of claim 7, wherein the heatable device includes a substrate, and the substrate has a thermal conductivity of below about 1.0 W/m° C.

11. The heating system of claim 7, wherein the heatable device includes a substrate, and the substrate includes a plastic material.

12. The heating system of claim 7, wherein the heatable device further comprises a sample cover including a surface that at least partially defines the reaction chamber.

13. The heating system of claim 12, wherein the sample cover surface defines at least one sidewall of the reaction chamber.

14. The heating system of claim 12, wherein the heatable device includes two sample covers that define at least two sidewalls of the reaction chamber.

15. The heating system of claim 12, wherein the sample cover has a thermal conductivity of greater than about 1.0 W/m° C., and an emissivity of about 0.1 or higher.

16. The heating system of claim 12, wherein the sample cover comprises an aluminum film blackened on at least a first side.

17. The heating system of claim 16, wherein the aluminum film has blackened by anodizing, painting, coating, or any combination thereof.

18. The heating system of claim 12, wherein the sample cover comprises a pigmented polycarbonate film material.

19. A heating system comprising:

a non-contact radiant heater;

a non-contact radiant temperature sensor;

a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor; and a biochemical sample including a nucleic acid sequence in the reaction chamber and sufficient components to enable at least one cycle of polymerase chain reaction of the nucleic acid sequence.

20. A heating system comprising:

a non-contact radiant heater;

a non-contact radiant temperature sensor; and a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the heatable device is spaced away from the non-contact radiant temperature sensor by a distance of from about five mm to about 20 mm.

21. A heating system comprising:

a non-contact radiant heater;

a non-contact radiant temperature sensor; and a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the heatable device is a microfluidic analytical device.

22. A heating system comprising:

a non-contact radiant heater;

a non-contact radiant temperature sensor; and a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the reaction chamber has at least one dimension that is less than or equal to 500 $\mu$m.

23. A heating system comprising:

a non-contact radiant heater;

a non-contact radiant temperature sensor; and a heatable device including a chemical reaction chamber having a volume of about 10 ml or less, the heatable device being spaced from the non-contact radiant heater spaced from the non-contact radiant temperature sensor, and positioned for the chemical reaction chamber to receive heat irradiated by the non-contact radiant heater and for the chemical reaction chamber to radiate heat toward the non-contact radiant temperature sensor, wherein the non-contact radiant temperature sensor has a field of view that falls within a surface of the reaction chamber.

24. A method of heating a biochemical sample comprising:

providing a heatable device that comprises a plurality of reaction chambers retaining a sample, the reaction chambers each having a volume of about 10 ml or less, a plurality of non-contact radiant heaters are provided, and a plurality of non-contact radiant temperature sensors are provided;

heating the plurality of reaction chambers with a plurality of non-contact radiant heaters spaced from the heatable device; and sensing temperatures of the plurality of reaction chambers with a plurality of non-contact temperature sensor spaced from the heatable device.

25. A method of heating a biochemical sample comprising:
- providing a heatable device that includes a reaction chamber retaining a sample, the reaction chamber having a volume of about 10 ml or less;
- heating the reaction chamber with a non-contact radiant heater spaced from the heatable device; and
- sensing a temperature of the reaction chamber with a non-contact temperature sensor spaced from the heatable device,
- wherein the heating comprises heating with laser-produced radiation.

26. A method of heating a biochemical sample comprising:
- providing a heatable device that includes a reaction chamber retaining a sample, the reaction chamber having a volume of about 10 ml or less;
- heating the reaction chamber with a non-contact radiant heater spaced from the heatable device; and
- sensing a temperature of the reaction chamber with a non-contact temperature sensor spaced from the heatable device,
- wherein the heating comprises heating with a halogen light source.

27. A method of heating a biochemical sample comprising:
- providing a heatable device that includes a reaction chamber retaining a sample, the reaction chamber having a volume of about 10 ml or less;
- heating the reaction chamber with a non-contact radiant heater spaced from the heatable device; and
- sensing a temperature of the reaction chamber with a non-contact temperature sensor spaced from the heatable device,
- wherein the non-contact radiant heater produces radiation having a wavelength of about 0.7 micrometer or longer.

28. A method of heating a biochemical sample comprising:
- providing a heatable device that includes a reaction chamber retaining a sample, the reaction chamber having a volume of about 10 ml or less, wherein the sample comprises a nucleic acid sequence and sufficient components to enable at least one cycle of polymerase chain reaction of the nucleic acid sequence;
- heating the reaction chamber with a non-contact radiant heater spaced from the heatable device;
- sensing a temperature of the reaction chamber with a non-contact temperature sensor spaced from the heatable device; and
- cycling the temperature of the reaction chamber in a manner sufficient to effect polymerase chain reaction of the nucleic acid sequence.

29. The method of claim 28, wherein cycling comprises:
- heating the reaction chamber to a temperature of about 95° C. with the non-contact radiant heater; and
- cooling the reaction chamber to a temperature of about 60° C., and maintaining the temperature at about 60° C.

30. The method of claim 29, further comprising the step of repeating the heating and cooling of the reaction chamber one or more times.

* * * * *